United States Patent
Kawaguchi et al.

(10) Patent No.: US 12,169,735 B2
(45) Date of Patent: Dec. 17, 2024

(54) ELECTRONIC DEVICE, CONTROL METHOD OF ELECTRONIC DEVICE, AND RECORDING MEDIUM

(71) Applicant: CASIO COMPUTER CO., LTD., Tokyo (JP)

(72) Inventors: Yohei Kawaguchi, Akishima (JP); Keiichi Nomura, Uenohara (JP); Fumiaki Ochiai, Higashiyamato (JP); Tatsuya Sekitsuka, Kunitachi (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 28 days.

(21) Appl. No.: 18/068,134

(22) Filed: Dec. 19, 2022

(65) Prior Publication Data
US 2023/0195508 A1     Jun. 22, 2023

(30) Foreign Application Priority Data
Dec. 21, 2021 (JP) .................................. 2021-207560

(51) Int. Cl.
*G06F 9/48* (2006.01)
*G06F 1/28* (2006.01)

(52) U.S. Cl.
CPC .............. *G06F 9/4818* (2013.01); *G06F 1/28* (2013.01)

(58) Field of Classification Search
CPC .................................. G06F 9/4818; G06F 1/28
See application file for complete search history.

(56) References Cited

U.S. PATENT DOCUMENTS

| | | | |
|---|---|---|---|
| 2006/0026330 A1* | 2/2006 | Yi .......................... | G06F 1/3203 710/309 |
| 2006/0149877 A1* | 7/2006 | Pearson .................. | G06F 13/24 710/260 |
| 2006/0229520 A1 | 10/2006 | Yamashita et al. | |
| 2007/0067652 A1* | 3/2007 | Asai ....................... | G06F 1/3253 713/300 |

(Continued)

FOREIGN PATENT DOCUMENTS

| JP | 2004230152 A | 8/2004 |
|---|---|---|
| JP | 2006312010 A | 11/2006 |

(Continued)

OTHER PUBLICATIONS

Notice of Reasons for Refusal dated Dec. 5, 2023 received in Japanese Patent Application No. JP 2021-207560.

*Primary Examiner* — Henry Tsai
*Assistant Examiner* — Harry Z Wang
(74) *Attorney, Agent, or Firm* — Scully, Scott, Murphy & Presser, P.C.

(57) ABSTRACT

An electronic device includes: a memory configured to a program; and one or more processors configured to execute the program stored in the memory. The one or more processors are connected to a first circuit and a second circuit, the first circuit being configured to execute a first operation cyclically and output an interrupt signal corresponding to the first operation, the second circuit being configured to execute a second operation in response to an operation instruction. In response to receiving the interrupt signal, the one or more processors output the operation instruction to the second circuit such that the second operation is not executed in a period in which the first operation affects the second operation.

17 Claims, 4 Drawing Sheets

(56) References Cited

U.S. PATENT DOCUMENTS

| | | | |
|---|---|---|---|
| 2007/0191719 A1 | 8/2007 | Yamashita et al. | |
| 2011/0004106 A1 | 1/2011 | Iwamiya et al. | |
| 2013/0111168 A1* | 5/2013 | Circello | G06F 9/526 |
| | | | 711/E12.098 |
| 2015/0286586 A1* | 10/2015 | Yadav | G06F 9/526 |
| | | | 711/152 |
| 2018/0173662 A1* | 6/2018 | Cho | G06F 13/4004 |
| 2019/0004983 A1* | 1/2019 | Mizumoto | G06F 13/1689 |

FOREIGN PATENT DOCUMENTS

| | | |
|---|---|---|
| JP | 5056867 B2 | 10/2012 |
| JP | 2015104428 A | 6/2015 |
| JP | 2017108905 A | 6/2017 |

* cited by examiner

ELECTRONIC DEVICE, CONTROL METHOD OF ELECTRONIC DEVICE, AND RECORDING MEDIUM

CROSS-REFERENCE TO RELATED APPLICATIONS

This application is based upon and claims the benefit of priority from Japanese Patent Application No. 2021-207560, filed on Dec. 21, 2021, the entire contents of which are incorporated herein by reference.

TECHNICAL FIELD

The disclosure of the present specification relates to an electronic device, a control method of an electronic device, and a recording medium.

BACKGROUND

An electronic device capable of detecting biological information has been known. For example, Japanese Patent Publication No. 5056867 discloses a specific configuration of this type of electronic device.

The electronic device disclosed in Japanese Patent Publication No. 5056867 causes a sensor to blink to obtain scattered light, and detects biological information such as a pulse wave based on the scattered light.

SUMMARY

An aspect of the present disclosure relates to an electronic device including: a memory configured to a program; and one or more processors configured to execute the program stored in the memory. The one or more processors are connected to a first circuit and a second circuit, the first circuit being configured to execute a first operation cyclically and output an interrupt signal corresponding to the first operation, the second circuit being configured to execute a second operation in response to an operation instruction. In response to receiving the interrupt signal, the one or more processors output the operation instruction to the second circuit such that the second operation is not executed in a period in which the first operation affects the second operation.

BRIEF DESCRIPTION OF DRAWINGS

Exemplary embodiments of the present invention will be described in detail based on the following figures, wherein.

DESCRIPTION OF EMBODIMENTS

An electronic device, a control method of an electronic device, and a recording medium according to an embodiment of the present disclosure will be described in detail with reference to the drawings.

Figure 1:
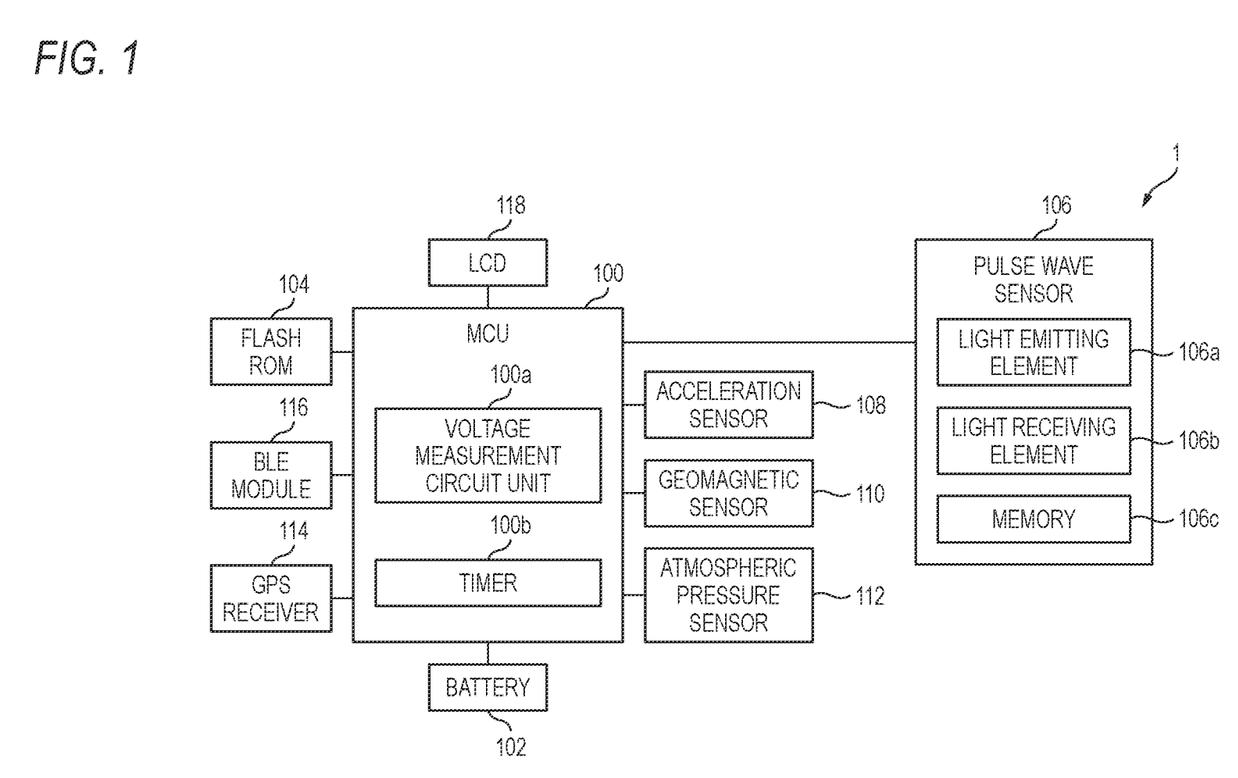
FIG. 1 is a block diagram illustrating a configuration of an electronic device according to an embodiment of the present disclosure.

FIG. 1 is a block diagram illustrating a configuration of an electronic device 1 according to the embodiment of the present disclosure. As illustrated in FIG. 1, the electronic device 1 can include an MCU 100, a battery 102, a flash ROM 104, a pulse wave sensor 106, an acceleration sensor 108, a geomagnetic sensor 110, an atmospheric pressure sensor 112, a global positioning system (GPS) receiver 114, a Bluetooth (registered trademark) low energy (BLE) module 116, and a liquid crystal display (LCD) 118.

The electronic device 1 is a wearable device that can be worn by a person. For example, the electronic device 1 is a wearable device used as a wrist watch, and can detect a pulse of a wrist of a wearer. The electronic device 1 described in the present embodiment is merely an example. The electronic device 1 may be a wearable device that is not used a wrist watch, or may be a device (for example, a smartphone and a tablet terminal) different from a wearable device.

MCU 100 is an element including a central processing unit (CPU), a read only memory (ROM), a random access memory (RAM), and the like. The MCU 100 reads a program and data stored in the ROM and uses the RAM as a work area, thereby controlling the electronic device 1. The MCU 100 is connected to circuit units illustrated in FIG. 1 via, for example, a bus.

The MCU 100 is, for example, a single-core processor having a single CPU core or a multi-core processor having plural CPU cores, and can include one or more processors. That is, the MCU 100 is an example of "one or more processors". When the MCU 100 includes plural processors, the MCU 100 may be packaged as a single device, or may be configured as plural physically separated devices in the electronic device 1.

The battery 102 is a power supply of the electronic device 1, and is, for example, a chargeable and dischargeable lithium ion battery. Electric power is supplied from the battery 102 to the units in the electronic device 1 through a power supply line. This enables the electronic device 1 to operate.

The flash ROM 104 is a nonvolatile semiconductor memory and serves as a secondary storage device or an auxiliary storage device. The flash ROM 104 stores, for example, data collected from the sensors.

The pulse wave sensor 106 is, for example, an optical pulse wave sensor, and can include a light emitting element 106a, a light receiving element 106b, and a memory 106c. The light emitting element 106a is, for example, a light emitting diode (LED) or a laser diode (LD).

The pulse wave sensor 106 is a sensor unit that measures a pulse wave of the wearer based on light emitted by the light emitting element 106a. For example, the pulse wave sensor 106 causes the light emitting element 106a to blink cyclically. The light emitted by the light emitting element 106a is irradiated to the wrist of the wearer wearing the electronic device 1, which is a wearable device used as a wrist watch. A wavelength of this light is, for example, a wavelength of green light in the vicinity of 550 nm at which absorbance of oxygenated hemoglobin in the artery is high. Therefore, the amount of scattered light from the wrist changes in accordance with a blood flow rate (in other words, a volume change of the artery) that changes with the pulsation of the heart. When the light receiving element 106b receives the scattered light, the pulse wave sensor 106 generates a signal corresponding to the amount of the received light and stores the signal in the memory 106c as pulse wave data.

The pulse wave sensor 106 transmits a predetermined interrupt signal to the MCU 100, for example, at a timing when the light emitting element 106a is caused to emit light. The interrupt signal is, for example, a signal for causing the MCU 100 to fetch the pulse wave data accumulated in the memory 106c. The interrupt signal may be transmitted to the MCU 100 whenever the light emitting element 106a emits light (in other words, every time one piece of the pulse wave data is obtained), or may be transmitted to the MCU 100 whenever the light emitting element 106a emits light plural times (in other words, every time plural pieces of pulse wave data are obtained).

As described above, the pulse wave sensor 106 is an example of a first circuit unit that executes a first operation (in the present embodiment, a light emitting operation by the light emitting element 106a) cyclically, and outputs a predetermined interrupt signal corresponding to the first operation.

The acceleration sensor 108 detects inertial forces in three axis directions orthogonal to one another, which is generated when a moving speed of the electronic device 1 (in other words, the wearer) changes, and transmits an electric signal corresponding to the detected inertial forces to the MCU 100. In addition, the geomagnetic sensor 110 detects values of magnetic forces in the three axis directions orthogonal to one another, and transmits an electric signal corresponding to values of the detected magnetic forces to the MCU 100. The MCU 100 estimates, for example, orientation, a moving direction, a moving speed, a moving distance and so on of the electronic device 1 based on electric signals input from the acceleration sensor 108 and the geomagnetic sensor 110.

The atmospheric pressure sensor 112 detects a pressure of the atmosphere and transmits an electric signal corresponding to the detected pressure to the MCU 100. The MCU 100 calculates an atmospheric pressure based on the electric signal input from the atmospheric pressure sensor 112.

The GPS receiver 114 receives radio wave signals from plural GPS satellites, and measures a position of the electronic device 1 based on the received radio wave signals. When the electronic device 1 is located in an area (for example, a tunnel or underground) where the GPS receiver 114 cannot receive a radio wave signal, the MCU 100 may estimate the position of the electronic device 1 by dead reckoning using the acceleration sensor 108 and the geomagnetic sensor 110, for example. The MCU 100 may estimate the position of the electronic device 1 by inputting output values of the acceleration sensor 108 and the geomagnetic sensor 110 and a positioning result of the GPS receiver 114 to a Kalman filter.

The BLE module 116 is a communication interface that wirelessly connects the electronic device 1 and an external device. The MCU 100 can transmit data collected from the sensors to an external device via the BLE module 116, for example. The electronic device 1 may include, for example, a communication interface conforming to the near field communication (NFC) standard or a communication interface conforming to the Wi-Fi standard, instead of or in addition to the BLE module 116.

The LCD 118 is, for example, a touch screen display, and serves as both a display unit and an operation part. The LCD 118 displays, for example, the pulse obtained by the pulse wave sensor 106, the moving distance and the like obtained by the acceleration sensor 108 and the geomagnetic sensor 110, the atmospheric pressure obtained by the atmospheric pressure sensor 112, and the current position obtained by the GPS receiver 114. The wearer can operate the electronic device 1 by touch interactions on the LCD 118.

The MCU 100 can include a voltage measurement circuit unit 100a, which is an example of a second circuit unit. The voltage measurement circuit unit 100a periodically measures a voltage of the battery 102. The MCU 100 estimates a remaining battery level based on the measured voltage. The estimated remaining battery level is displayed on, for example, the LCD 118. The wearer can determine whether to charge the electronic device 1, for example, by visually recognizing the remaining battery level displayed on the LCD 118. The voltage measurement circuit unit 100a may be configured as another circuit unit that operates under the control of the MCU 100 and that is physically separated from the MCU 100.

Here, the MCU 100 cannot output a clock to other circuit units. Therefore, circuit units such as the pulse wave sensor 106 operate asynchronously with the MCU 100. Since the MCU 100 operates asynchronously with the circuit units, for example, when the voltage measurement circuit unit 100a measures the voltage of the battery 102 at a timing when a large current is consumed due to operations of the circuit units, an accurate measurement value may not be obtained. This is because, when a large current is consumed due to the operations of the circuit units, the voltage of the battery 102 temporarily drops.

Therefore, in the present embodiment, the electronic device 1 executes the following processing. By executing this processing, the measurement accuracy of the voltage of the battery 102 is improved.

Figure 2:
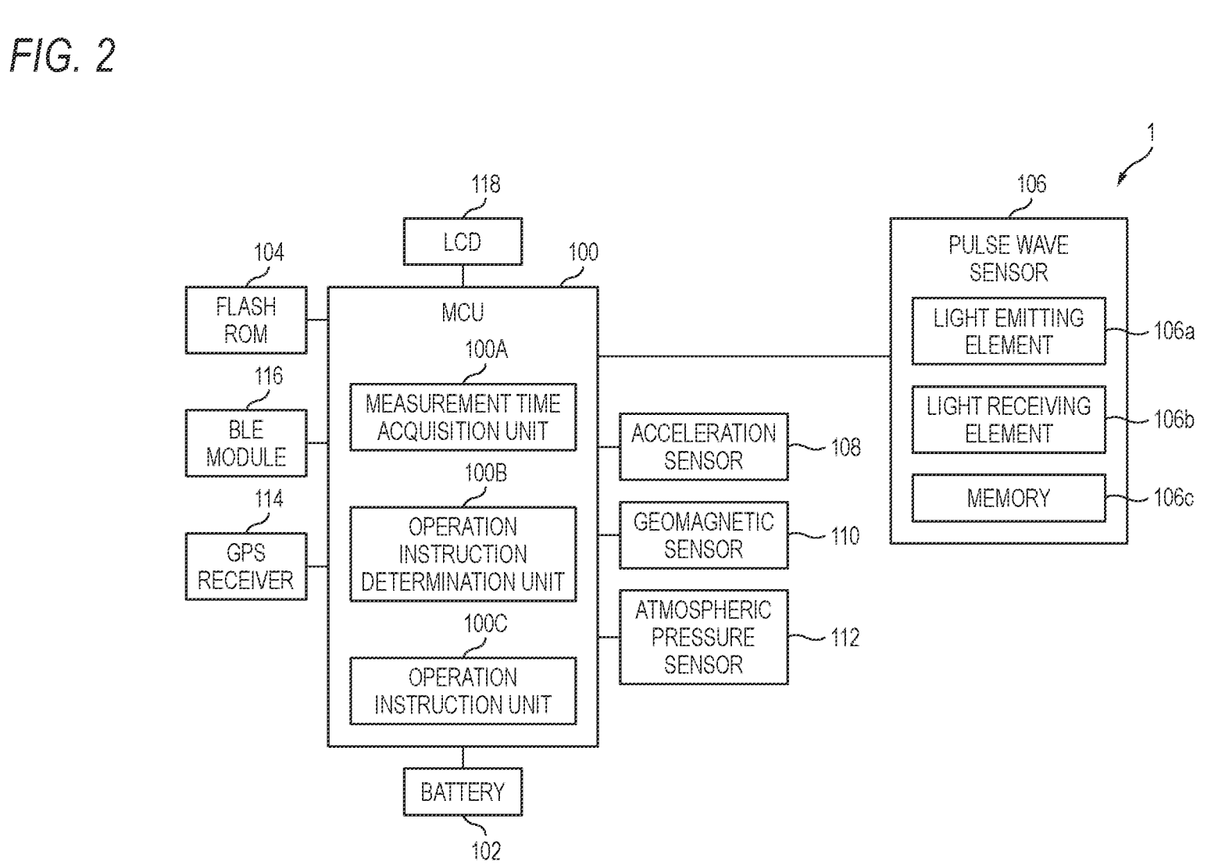
FIG. 2 is a diagram for illustrating a processing of improving measurement accuracy of a voltage of a battery provided in the electronic device according to the embodiment of the present disclosure.
Figure 3:
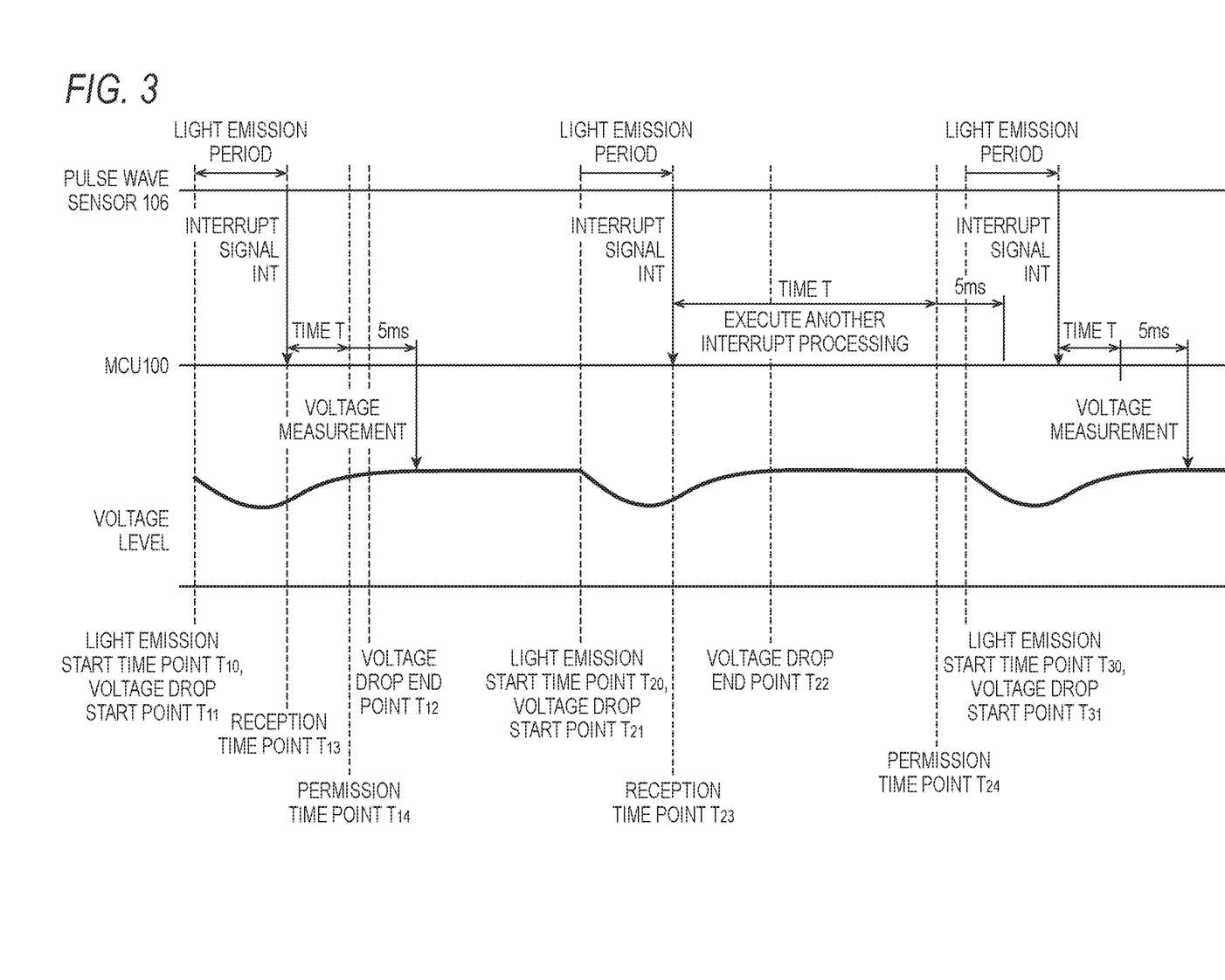
FIG. 3 is a timing chart illustrating, on a time axis, operations of a pulse wave sensor and a micro controller unit (MCU) provided in the electronic device according to the embodiment of the present disclosure, and a voltage level of the battery.

FIGS. 2 and 3 are diagrams for illustrating the processing of improving the measurement accuracy of the voltage of the battery 102. FIG. 2 is a diagram illustrating a functional block configuration of the MCU 100. FIG. 3 is a timing chart illustrating operations of the pulse wave sensor 106 and the MCU 100 and a voltage level of the battery 102 on a time axis.

The MCU 100 can include a measurement time acquisition unit 100A, an operation instruction determination unit 100B, and an operation instruction unit 100C as functional blocks. In the examples in FIGS. 2 and 3, an operation instruction (a predetermined operation instruction) is output to the voltage measurement circuit unit 100a, such that the operations of these functional blocks do not cause a voltage measurement operation by the voltage measurement circuit unit 100a to be executed in a period in which the voltage of the battery 102 temporarily drops due to the light emitting operation by the light emitting element 106a.

In the present embodiment, each functional block of the MCU 100 is implemented by a program executed by the MCU 100 that is an example of a computer. Some or all of the functional blocks may be implemented by hardware such as a dedicated logic circuit.

The voltage measurement operation by the voltage measurement circuit unit 100a is an operation for measuring the voltage of the battery 102 that supplies power to the electronic device 1, and is an example of a second operation. The light emitting operation by the light emitting element 106a is an operation having a higher load on the power supply than the second operation, and is an example of the first operation.

As described above, by outputting the operation instruction to the voltage measurement circuit unit 100a, it is possible to prevent an operation by a circuit unit such as the sensor from affecting an operation result of another circuit unit. For example, the measurement of the voltage of the battery 102 at the time when a temporary voltage drop occurs due to the light emitting operation by the light emitting element 106a is avoided. The voltage measurement circuit unit 100a can measure the voltage of the battery 102 at a timing when the temporary voltage drop is not occurring. Therefore, the measurement accuracy of the voltage of the battery 102 is improved.

As illustrated in FIG. 3, the pulse wave sensor 106 causes the light emitting element 106a to blink at a constant cycle. Every time the light emitting element 106a is caused to emit light, the pulse wave sensor 106 obtains pulse wave data and stores the pulse wave data in the memory 106c, and outputs an interrupt signal INT to the MCU 100. The interrupt signal INT is an interrupt signal for causing the MCU 100 to fetch the pulse wave data accumulated in the memory 106c.

As illustrated in FIG. 3, when the light emitting element 106a emits light in the pulse wave sensor 106, the voltage of the battery 102 temporarily drops.

As illustrated in FIG. 2, the MCU 100 can include a timer 100b serving as a time counting unit. When the interrupt signal INT is received by the MCU 100, the timer 100b is automatically activated. The activated timer 100b starts counting up with a reception time-point of the interrupt signal INT as a base point.

The MCU 100 permits (in other words, recognizes) the interrupt signal INT, for example, several milliseconds after receiving the interrupt signal INT.

For convenience, in FIG. 3, a first light emission start time-point of the light emitting element 106a is referred to as a "light emission start time-point T10", and a start point and an end point of a voltage drop period of the battery 102 that corresponds to the light emission start time-point T10 are referred to as a "voltage drop start point T11" and a "voltage drop end point T12", respectively. A reception time-point and a permission time-point of the first interrupt signal INT are referred to as a "reception time-point T13" and a "permission time-point T14", respectively. In FIG. 3, in a second round, the light emission start time-point of the light emitting element 106a is referred to as a "light emission start time-point T20", and the start point and the end point of the voltage drop period of the battery 102 that corresponds to the light emission start time-point T20 are referred to as a "voltage drop start point T21" and a "voltage drop end point T22", respectively. In the second round, the reception time-point and the permission time-point of the interrupt signal INT are referred to as a "reception time-point T23" and a "permission time-point T24", respectively. Further, in FIG. 3, in a third round, the light emission start time-point of the light emitting element 106a is referred to as a "light emission start time-point T30", and the start point of the voltage drop period of the battery 102 corresponding to the light emission start time-point T30 is referred to as a "voltage drop start point T31". The voltage drop period of the battery 102 is an example of a period in which the first operation affects the second operation.

Figure 4:
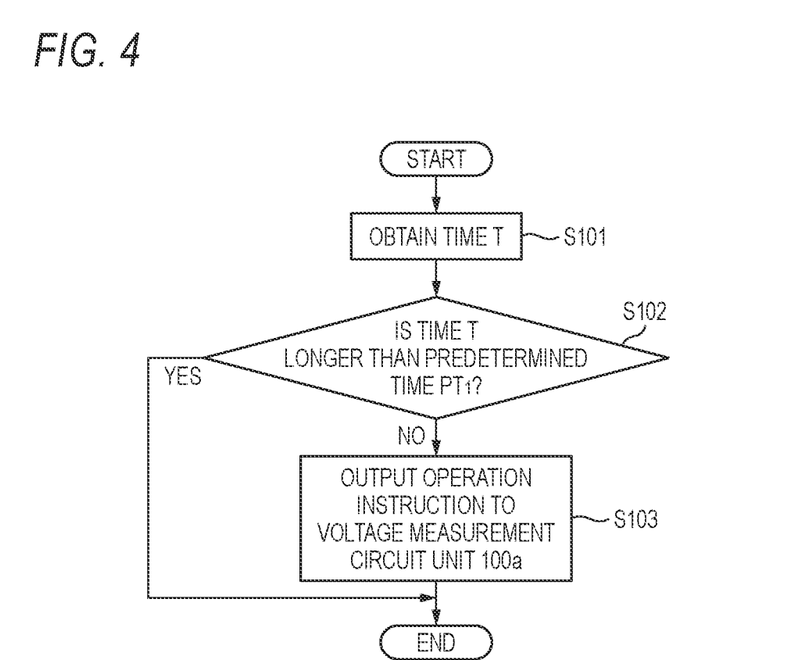
FIG. 4 is a flowchart illustrating a program executed by the MCU in the embodiment of the present disclosure.

FIG. 4 is a flowchart illustrating a program (and a method) executed by the MCU 100 in the embodiment of the present disclosure. For example, when the interrupt signal INT is permitted, the MCU 100 starts the execution of the processing illustrated in FIG. 4. When the interrupt signal INT is permitted, the MCU 100 performs a processing of fetching the pulse wave data stored in the memory 106c of the pulse wave sensor 106, for example, in parallel with the processing illustrated in FIG. 4.

As illustrated in FIG. 4, the MCU 100 obtains a time T until the permission time-point of the interrupt signal INT that is measured by the timer 100b (step S101). That is, the MCU 100 operates as the measurement time acquisition unit 100A that obtains the time T lasting from the reception of the interrupt signal INT to the permission of the interrupt signal INT. For example, after the time T is obtained by the MCU 100, the timer 100b is stopped, and a count value thereof is reset.

The MCU 100 determines whether the time T obtained in step S101 is longer than a predetermined time PT1 (step S102).

Here, the MCU 100 may receive an interrupt signal from a circuit unit other than the pulse wave sensor 106. The priority of each interrupt signal (in other words, each interruption processing) is set by, for example, a controller (not illustrated) for the interruption processing. While the MCU 100 is executing an interruption processing set with a high priority, the MCU 100 does not permit an interruption processing set with a lower priority. Therefore, the time T until the permission of the interrupt signal INT varies depending on a processing status of the MCU 100 at the time of reception of the interrupt signal INT.

In FIG. 3, at the reception time-point T13, the MCU 100 is not executing an interruption processing having a priority higher than a priority of an interruption processing (that is, a pulse wave data fetching processing) corresponding to the interrupt signal INT. Therefore, the MCU 100 permits the interrupt signal INT immediately after receiving the interrupt signal INT. In this case, the time T obtained in step S101, that is, the elapsed time from the reception time-point T13 to the permission time-point T14 is equal to or shorter than the predetermined time PT1.

When the time T is equal to or shorter than the predetermined time PT1 (step S102: NO), there is a sufficient time from the current time-point (that is, the permission time-point T14) to the next voltage drop start point T21. Therefore, if the voltage measurement operation by the voltage measurement circuit unit 100a is quickly executed, an execution period of the voltage measurement operation does not overlap the next voltage drop period of the battery 102.

Therefore, the MCU 100 outputs an operation instruction to the voltage measurement circuit unit 100a so as to measure the voltage of the battery 102 after elapse of a predetermined time PT2 (for example, 5 milliseconds) from the current time-point (that is, the permission time-point T14) (step S103). Accordingly, the voltage measurement operation by the voltage measurement circuit unit 100a is executed outside the voltage drop period of the battery 102 due to the light emitting operation by the light emitting element 106a. Therefore, it is possible to obtain an accurate measurement value. It is possible for the MCU 100 to estimate the remaining battery level with high accuracy.

If the voltage measurement circuit unit 100a is caused to measure the voltage of the battery 102 immediately after the permission time-point T14, the voltage measurement operation is executed in some cases at a timing (that is, a timing when the voltage drop period is not ended) that temporally overlaps the first voltage drop period (that is, a period from the voltage drop start point T11 to the voltage drop end point T12). In order to more reliably avoid such a problem, in the present embodiment, the voltage measurement circuit unit 100a is caused to measure the voltage of the battery 102 not immediately after the permission time-point T14 but after elapse of the predetermined time PT2.

As described above, in step S103, the MCU 100 determines a timing at which the voltage measurement circuit unit 100a is caused to perform the voltage measurement operation, based on the elapsed time (time T) from the reception time-point T13 to the permission time-point T14. Namely, it can be said that the MCU 100 determines the timing, at which the voltage measurement circuit unit 100a is caused to perform the voltage measurement operation, based on a timing at which the interrupt signal INT is received (that is, the reception time-point T13). In addition, it can be said that the timing at which the voltage measurement circuit unit 100a is caused to perform the voltage measurement operation is determined based on a timing at which the interrupt signal INT is permitted (that is, the permission time-point T14).

In FIG. 3, at the reception time-point T23, the MCU 100 is executing an interruption processing having a higher priority than a priority of the pulse wave data fetching processing. The MCU 100 does not permit the interrupt signal INT until all the interruption processing having a higher priority than the priority of the pulse wave data fetching processing are completed. In this case, the time T obtained in step S101, that is, the elapsed time from the reception time-point T23 to the permission time-point T24 is longer than the predetermined time PT1.

When the time T is longer than the predetermined time PT1 (step S102: YES), the time from the current time-point (that is, the permission time-point T24) to the next voltage drop start point T31 is not sufficient. Therefore, even when the voltage measurement operation by the voltage measurement circuit unit 100a is quickly executed, there is a high possibility that the execution period of the voltage measurement operation overlaps the next voltage drop period of the battery 102.

Therefore, the MCU 100 ends the processing illustrated in the flowchart of FIG. 4 without outputting an operation instruction to the voltage measurement circuit unit 100a. Accordingly, it is possible to avoid the measurement of the voltage of the battery 102 during the voltage drop period of the battery 102 due to the light emitting operation by the light emitting element 106a.

As described above, in steps S102 and S103, the MCU 100 operates as the operation instruction determination unit 100B that determines, based on the time T obtained in step S101, whether to output an operation instruction to the voltage measurement circuit unit 100a. In step S103, the MCU 100 operates as the operation instruction unit 100C that outputs an operation instruction to the voltage measurement circuit unit 100a.

The predetermined time PT2 (5 milliseconds in the present embodiment) from when the MPU 100 permits the interrupt signal INT to when the voltage measurement circuit unit 100a performs the voltage measurement operation is an example of a first predetermined time. In order to more reliably avoid the overlap between the execution period of the voltage measurement operation and the voltage drop period of the battery 102, the predetermined time PT2 is set in advance based on, for example, the following items (1) to (3).

(1) Priority of interrupt signal INT
(2) Cycle in which the light emitting operation by the light emitting element 106a is executed
(3) A period in which the light emitting operation affects the voltage measurement operation (that is, a voltage drop period of the battery 102)

The predetermined time PT1 for determining whether to output an operation instruction to the voltage measurement circuit unit 100a is an example of a second predetermined time. In order to more reliably avoid the overlap between the execution period of the voltage measurement operation and the voltage drop period of the battery 102, the predetermined time PT1 is set in advance based on, for example, the above items (1) to (3) and the predetermined time PT2.

As described above, according to the present embodiment, there are provided an electronic device, a control method of an electronic device, and a recording medium that are capable of preventing an operation by a circuit unit such as a sensor from affecting an operation result of another circuit unit.

In addition, the present disclosure is not limited to the embodiment described above, and various modifications can be made without departing from the gist of the present disclosure in an implementation stage. In addition, the functions implemented in the above-described embodiment may be appropriately combined as much as possible. The embodiment described above include various stages, and various inventions can be extracted by appropriately combining plural disclosed constituent elements. For example, even if some constituent elements are deleted from all the constituent elements shown in the embodiment, a configuration in which the constituent elements are deleted can be extracted as an invention as long as the effect can be obtained.

Although the light emitting operation by the light emitting element 106a and the voltage measurement operation by the voltage measurement circuit unit 100a are described respectively as the first operation and the second operation in the above-described embodiment, the configuration of the present disclosure is not limited thereto. For example, an operation by a circuit unit different from the pulse wave sensor 106 may temporarily cause the voltage of the battery 102 to drop. Also in this case, for example, when the MPU 100 receives an interrupt signal from the corresponding circuit unit, the MPU 100 outputs an operation instruction to the voltage measurement circuit unit 100a so that the voltage measurement operation is not executed during the voltage drop period of the battery 102. Accordingly, the measurement accuracy of the voltage of the battery 102 is improved.

The invention claimed is:

1. An electronic device, comprising:
a memory configured to store a program;
one or more processors configured to execute the program stored in the memory;
a first circuit; and
a second circuit,
wherein the one or more processors are connected to the first circuit and the second circuit, the first circuit being configured to execute a first operation cyclically and output an interrupt signal corresponding to the first operation, the second circuit being configured to execute a second operation in response to an operation instruction,
in response to receiving the interrupt signal, the one or more processors output the operation instruction to the second circuit such that the second operation is not executed in a period in which the first operation affects the second operation,
the electronic device is a wearable device,
the first circuit is a sensor that includes a light emitting element and that is configured to measure a pulse wave of a wearer based on light emitted by the light emitting element, and
the first operation is a light emitting operation by the light emitting element.

2. The electronic device according to claim 1, wherein the one or more processors are configured to determine a timing, at which the second circuit is caused to perform the second operation, based on a timing at which the interrupt signal is received.

3. The electronic device according to claim 1, wherein the one or more processors are configured to permit the interrupt signal after receiving the interrupt signal, and determine a timing, at which the second circuit is caused to perform the second operation, based on a timing at which the interrupt signal is permitted.

4. The electronic device according to claim 3, wherein
the one or more processors cause the second circuit to perform the second operation after elapse of a first time from permission of the interrupt signal, and
the first time is set based on a priority of the interrupt signal, a cycle in which the first operation is executed, and a period in which the first operation affects the second operation.

5. The electronic device according to claim 3, wherein the one or more processors are configured to measure a time lasting from reception of the interrupt signal to permission of the interrupt signal, and determine whether to output the operation instruction based on the measured time.

6. The electronic device according to claim 5, wherein the one or more processors do not output the operation instruction when the measured time is longer than a second time.

7. The electronic device according to claim 6, wherein the second time is set based on a priority of the interrupt signal, a cycle in which the first operation is executed, a period in which the first operation affects the second operation, and a time from when the one or more processors permit the interrupt signal to when the second operation is performed by the second circuit.

8. An electronic device, comprising:
a memory configured to store a program; and
one or more processors configured to execute the program stored in the memory, wherein the one or more processors are connected to a first circuit and a second circuit, the first circuit being configured to execute a first operation cyclically and output an interrupt signal corresponding to the first operation, the second circuit being configured to execute a second operation in response to an operation instruction,
in response to receiving the interrupt signal, the one or more processors output the operation instruction to the second circuit such that the second operation is not executed in a period in which the first operation affects the second operation,
the second operation is an operation for measuring a voltage of a battery that supplies power to the electronic device, and
the first operation is an operation having a higher load on a power supply than the second operation.

9. A control method of an electronic device to be executed by a computer wherein the computer is connected to a first circuit and a second circuit, the first circuit being configured to execute a first operation cyclically and output an interrupt signal corresponding to the first operation, the second circuit being configured to execute a second operation in response to an operation instruction, the control method comprises:
in response to receiving the interrupt signal, outputting the operation instruction to the second circuit such that the second operation is not executed in a period in which the first operation affects the second operation,
the electronic device is a wearable device,
the first circuit is a sensor that includes a light emitting element and that is configured to measure a pulse wave of a wearer based on light emitted by the light emitting element, and
the first operation is a light emitting operation by the light emitting element.

10. The control method of the electronic device according to claim 9, further comprising:
determining a timing, at which the second circuit is caused to perform the second operation, based on a timing at which the interrupt signal is received.

11. The control method of the electronic device according to claim 9, further comprising:
permitting the interrupt signal after receiving the interrupt signal; and
determining a timing, at which the second circuit is caused to perform the second operation, based on a timing at which the interrupt signal is permitted.

12. The control method of the electronic device according to claim 11, further comprising:
causing the second circuit to perform the second operation after elapse of a first time from permission of the interrupt signal, wherein
the first time is set based on a priority of the interrupt signal, a cycle in which the first operation is executed, and a period in which the first operation affects the second operation.

13. The control method of the electronic device according to claim 11, further comprising:
measuring a time lasting from reception of the interrupt signal to permission of the interrupt signal; and
determining whether to output the operation instruction based on the measured time.

14. The control method of the electronic device according to claim 13, wherein the computer does not output the operation instruction when the measured time is longer than a second time.

15. The control method of the electronic device according to claim 14, wherein the second time is set based on a priority of the interrupt signal, a cycle in which the first operation is executed, a period in which the first operation affects the second operation, and a time from when permitting the interrupt signal to when the second operation is performed by the second circuit.

16. The control method of the electronic device according to claim 9, wherein
the second operation is an operation for measuring a voltage of a battery that supplies power to the electronic device, and
the first operation is an operation having a higher load on a power supply than the second operation.

17. A control method of an electronic device to be executed by a computer,
wherein the computer is connected to a first circuit and a second circuit, the first circuit being configured to execute a first operation cyclically and output an interrupt signal corresponding to the first operation, the second circuit being configured to execute a second operation in response to an operation instruction, and
wherein the control method comprises:
in response to receiving the interrupt signal, outputting the operation instruction to the second circuit such that the second operation is not executed in a period in which the first operation affects the second operation,
the second operation is an operation for measuring a voltage of a battery that supplies power to the electronic device, and
the first operation is an operation having a higher load on a power supply than the second operation.

* * * * *

UNITED STATES PATENT AND TRADEMARK OFFICE
CERTIFICATE OF CORRECTION

PATENT NO. : 12,169,735 B2
APPLICATION NO. : 18/068134
DATED : December 17, 2024
INVENTOR(S) : Yohei Kawaguchi et al.

Page 1 of 1

It is certified that error appears in the above-identified patent and that said Letters Patent is hereby corrected as shown below:

In the Claims

Column 9, Claim 9, Line 48, should read:
by a computer, wherein the computer is connected to a first Signed and Sealed this
Seventeenth Day of June, 2025

Coke Morgan Stewart
*Acting Director of the United States Patent and Trademark Office*